United States Patent [19]
Correia et al.

[11] Patent Number: 5,637,781
[45] Date of Patent: Jun. 10, 1997

[54] PROCESS FOR THE ALCOHOLYSIS OF CARBON TETRACHLORIDE

[75] Inventors: Yves Correia; Noel Fino, both of Chateau Arnoux; Philippe Leduc, Saint Auban, all of France

[73] Assignee: Elf Atochem S.A., Puteaux, France

[21] Appl. No.: 465,336

[22] Filed: Jun. 5, 1995

[30] Foreign Application Priority Data

Jun. 6, 1994 [FR] France .................. 94 06890

[51] Int. Cl.$^6$ .................................................. C07C 17/16
[52] U.S. Cl. ...................................... 570/261; 570/258
[58] Field of Search ............................. 570/261, 258

[56] References Cited

U.S. PATENT DOCUMENTS

| | | | |
|---|---|---|---|
| 2,172,568 | 9/1939 | Rothweiler | 260/652 |
| 2,871,256 | 1/1959 | Ivins et al. | 260/475 |
| 4,073,816 | 2/1978 | Herrmann | 570/258 |
| 5,196,618 | 3/1993 | Okon et al. | 570/258 |
| 5,227,550 | 7/1993 | Shimizu | 570/258 |

*Primary Examiner*—Alan Siegel
*Attorney, Agent, or Firm*—Millen, White, Zelano, & Branigan, P.C.

[57] ABSTRACT

The invention relates to a process for the alcoholysis of carbon tetrachloride which consists in simultaneously sending, on the one hand, carbon tetrachloride and, on the other hand, an alcohol ROH, over a catalytic composition, characterized in that the said catalytic composition comprises an aqueous solution of a metal halide.

15 Claims, No Drawings

PROCESS FOR THE ALCOHOLYSIS OF CARBON TETRACHLORIDE

BACKGROUND OF THE INVENTION

The present invention relates to a process for the alcoholysis of carbon tetrachloride ($CCl_4$) in the presence of an aqueous solution of a metal halide.

The reaction for the alcoholysis of $CCl_4$ according to the equation:

$$4ROH + CCl_4 \rightarrow 4RCl + 2H_2O + CO_2 \qquad (I)$$

leads to alkyl halides RCl and allows the $CCl_4$ to be upgraded. $CCl_4$ is inevitably produced in the manufacture of higher chloromethanes, but the use of $CCl_4$ as a commodity chemical will likely be banned at the end of this century since it is highly suspected of being responsible for the decrease of the ozone layer in the stratosphere.

French patent 793,731 describes a process for the alcoholysis of $CCl_4$ which consists in passing a gaseous mixture consisting of an alcohol (ethanol or methanol) and $CCl_4$ over solid substances having an active surface such as active charcoal or silica gel. These substances may optionally be charged with activating substances such as zinc chloride ($ZnCl_2$) or phosphorus compounds.

European Patent Application EP 435,210 describes a process for the preparation of $CH_3Cl$ which consists in passing a gaseous mixture consisting of $CH_3OH$ and $CCl_4$ over a solid catalytic bed of active charcoal containing an oxide or a halide of an element chosen from groups I B, II A, II B, VI B, VII B and VIII of the Periodic Table of the Elements. The reaction takes place at temperatures between 150° C. and 250° C. at pressures equal to about 10 kg/cm².

German patent DE 4,131,213 describes a process for the alcoholysis of $CCl_4$ which consists in reacting, in the gaseous phase, $CCl_4$ with an aliphatic alcohol having from 1 to 10 carbon atoms, in the presence of a solid catalyst which consists of silica and/or activated alumina.

SUMMARY OF THE INVENTION

A process has now been found for the alcoholysis of carbon tetrachloride which comprises simultaneously sending, on the one hand, $CCl_4$ and, on the other hand, at least one alcohol, ROH, in which R represents a linear or branched alkyl radical having a number of carbon atoms ranging from 1 to 10, over a catalytic composition, characterized in that the said catalytic composition comprises an aqueous solution of a metal halide.

According to the present invention, the metal halide is chosen from halides of the metals of groups I B (e.g., copper), II B (e.g., zinc and cadmium), VI B (e.g., chromium and molybdenum) and VIII (e.g., iron, cobalt and nickel) of the Periodic Table of the Elements.

Among these metal halides, it is preferred to use the metal chlorides and, most particularly, zinc chloride, $ZnCl_2$.

Examples of alcohols, ROH, which may be used according to the present invention, include but are not limited to: methanol, ethanol, propanol, butanol, isopropanol and mixtures thereof.

The weight concentration of metal halide in the catalytic composition is at most equal to 98% and preferably between 50% and 90%.

The reaction may advantageously be performed at a pressure at most equal to 10 bar and preferably between 3 and 5 bar.

According to the present invention, the reaction may be carried out at a temperature at most equal to 250° C. and preferably between 150° C. and 200° C.

The reactants may be introduced into the catalytic composition in the vapour state and/or in the liquid state.

The residence time, calculated as being the ratio of the total volume of the catalytic composition to the total volume of the mixture of the gaseous reactants per unit time under the pressure and temperature conditions as defined above, is between 10 and 60 seconds.

The ROH/$CCl_4$ molar ratio may vary within a wide range. It may be less than, equal to or greater than the stoichiometry of equation (I) depending on whether it is desired to have an excess of one or other of the reactants.

The reaction for the alcoholysis of $CCl_4$ may also be accompanied by a simultaneous equilibrium reaction of dehydration of the alcohol ROH into dialkyl ether ROR, according to the equation

$$2\,ROH \rightleftharpoons ROR + H_2O \qquad (II)$$

According to the present invention, this equilibrium may be displaced favourably if the ether formed is recycled with the reactant mixture.

It would not be departing from the scope of the invention if the alcohols ROH were simultaneously hydrochlorinated, with the same catalytic composition and under the same operating conditions of pressure and temperature, according to the equation:

$$ROH + HCl \rightarrow RCl + H_2O \qquad (III)$$

According to this variant, it is preferred to introduce the hydrogen chloride in gaseous form and in an amount such that it is in excess relative to the stoichiometry of equation (III).

This excess may vary within a wide range and may be up to 30%, but is preferably between 10% and 20%.

If the alcoholysis of $CCl_4$ and the hydrochlorination of the alcohols are carried out simultaneously, in the molar ratio

$$\frac{ROH}{CCl_4}$$

"ROH" represents the number of moles of ROH entering into the reaction (I) plus the number of moles of ROH entering into the reaction (III).

The process of the present invention applies to the preparation of alkyl chlorides such as $CH_3Cl$, $CH_3CH_2Cl$ and $CH_3(CH_2)_2Cl$ or a mixture thereof.

It applies most particularly to the manufacture of $CH_3Cl$ by methanolysis of $CCl_4$.

According to the second variant of the process, the hydrochlorination of methanol according to equation (III) may be performed at the same time as the methanolysis of $CCl_4$ according to equation (I).

At the outlet of the reactor containing the catalytic composition, the products are recovered by means known to those skilled in the art, namely, depressurization, cooling and then one or more distillations in order to separate the products obtained from the unconverted reactants which, if need be, may be recycled.

The process according to the present invention has the advantage of converting $CCl_4$ almost entirely into RCl without the interfering formation of side products which would necessitate expensive separations.

Without further elaboration, it is believed that one skilled in the art can, using the preceding description utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, and above and below, and of corresponding French application 94/06890, are hereby incorporated by reference.

EXAMPLE 1

50 ml of a 90% solution of zinc chloride in water are placed in a 150 ml glass laboratory reactor heated externally by an oil bath and equipped with a dip tube, a vent, a connection for measuring the temperature and a magnetic stirrer. While the bath temperature is maintained at 180° C. and the reactor is maintained at 3.8 bar effective, a mixture of methanol and $CCl_4$ is introduced continuously at a rate of 36 g/h (the residence time is equal to 36 seconds) in the $MeOH/CCl_4$ molar ratio=4, and the gases exiting the reactor are analysed and measured. It is observed that 19.8 g of methyl chloride and 4.3 g of carbon dioxide are produced per hour, unreacted $CCl_4$ and methanol being present at the outlet. The amounts measured correspond to a degree of conversion for the $CCl_4$ of 77%.

EXAMPLE 2

A methanol/carbon tetrachloride mixture in a molar ratio of 95/5 and hydrogen chloride are simultaneously introduced, such that the hydrogen chloride is in a theoretical stoichiometric excess of about 13%, into the catalytic composition consisting of an aqueous 70% solution of $ZnCl_2$, at a temperature of 160°–170° C. and at a pressure of 3.5 bar, in an industrial unit for the preparation of methyl chloride by the process for the hydrochlorination of methanol using hydrogen chloride.

The inlet-outlet balance of the industrial reactor is as follows:

|  | Inlet (kg/h) | Outlet (kq/h) |
|---|---|---|
| $CH_3OH$ | 4535 | 135 |
| $CCl_4$ | 1091 | 0 |
| HCl | 4737 | 752 |
| $H_2O$ | 0 | 2221 |
| $CH_3Cl$ | 0 | 6943 |
| $CO_2$ | 0 | 312 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A catalytic process for the alcoholysis of carbon tetrachloride comprising simultaneously contacting, $CCl_4$ and at least one alcohol ROH in which R represents a linear or branched alkyl radical having 1–10 carbon atoms with a catalytic composition consisting essentially of an aqueous solution of a metal halide.

2. A process according to claim 1, wherein the metal halide is chosen from halides of the metals of groups I B, II B, VI B and VIII of the Periodic Table of the Elements.

3. A process according to claim 2, wherein the metal halide is a metal chloride.

4. A process according to claim 3, wherein the metal chloride is zinc chloride, $ZnCl_2$.

5. A process according claim 1, wherein the weight concentration of metal halide in the catalytic composition is at most equal to 98%.

6. A process according to claim 5, wherein the weight concentration of metal halide in the catalytic composition is between 50% and 90%.

7. A process according to claim 1, wherein the reaction is carried out at a temperature at most equal to 250° C.

8. A process according to claim 7, wherein the reaction is carried out a temperature between 150° C. and 200° C.

9. A process according to claim 7, wherein the reaction is performed at a pressure at most equal to 10 bar.

10. A process according to claim 8, wherein the reaction is performed at a pressure between 3 and 5 bar.

11. A process according to claim 1, wherein the alcoholysis of carbon tetrachloride and the hydrochlorination of at least one alcohol ROH are carried out simultaneously.

12. A process according to claim 11, wherein the alcohol is methanol.

13. A process according to claim 1 for the preparation of methyl chloride.

14. A process according to claim 6, wherein the metal halide is zinc chloride.

15. A process according to claim 1, wherein the $CCl_4$ and the at least one alcohol ROH are introduced into the catalytic composition in the liquid state.

* * * * *